United States Patent [19]

Kramer

[11] Patent Number: 5,685,717
[45] Date of Patent: Nov. 11, 1997

[54] DENTAL PORCELAIN SHADING KIT, SYSTEM AND METHOD

[75] Inventor: Carolyn M. Kramer, Moorestown, N.J.

[73] Assignee: Ceramco Inc., Burlington, N.J.

[21] Appl. No.: 456,151

[22] Filed: May 31, 1995

Related U.S. Application Data

[62] Division of Ser. No. 257,411, Jun. 9, 1994, Pat. No. 5,482,732.

[51] Int. Cl.$^6$ ............................................. A61C 13/08
[52] U.S. Cl. ...................... 433/203.1; 206/63.5; 427/2.29
[58] Field of Search ................... 433/203.1; 427/2.29, 427/419.4, 140, 142, 379; 206/63.5

[56] References Cited

U.S. PATENT DOCUMENTS

| | | | |
|---|---|---|---|
| 3,628,260 | 12/1971 | Jacobsen | 35/28.5 |
| 4,426,404 | 1/1984 | Shoher et al. | 427/2.29 |
| 4,461,618 | 7/1984 | DeLuca et al. | 427/2.29 |
| 4,604,366 | 8/1986 | Kacicz et al. | 501/6 |
| 4,806,383 | 2/1989 | Poltz | 427/2 |
| 4,810,193 | 3/1989 | Wieder | 433/26 |
| 4,828,117 | 5/1989 | Panzera et al. | 206/63.5 |
| 4,879,136 | 11/1989 | Polz | 427/2 |
| 4,937,928 | 7/1990 | van der Zel | 29/160.6 |
| 5,173,114 | 12/1992 | Heurtaux | 106/35 |
| 5,314,334 | 5/1994 | Panzera et al. | 433/206 |

*Primary Examiner*—Cary E. O'Connor
*Attorney, Agent, or Firm*—Dale R. Lovercheck; James B. Bieber

[57] ABSTRACT

The invention provides a kit, system and method for the preparation of porcelain dental restorations. First, second and third powders are provided in labeled containers. The first powder has a lightness value ($L_1$) when formed into a least opaque porcelain layer. The second powder has a lightness value ($L_2$) when formed into a less opaque ceramic layer. The third powder has a lightness value ($L_3$) when formed into a most opaque ceramic layer. The third lightness value is greater than the second lightness value, which is greater than the first lightness value. The lightness value differences between the third lightness value ($L_3$) and the first lightness value ($L_1$) are less than 2.5 CIE L*a*b units. Preferably, the first powder has a first hue ($H_1$) when formed into the least opaque porcelain layer, the second powder has a second hue ($H_2$) when formed into the less opaque ceramic layer, and the third powder has a third hue ($H_3$) when formed into the most opaque ceramic layer. Preferably the first hue ($H_1$) and the second hue ($H_2$) are within 5 degrees of the CIE psychometric hue angle of the third hue ($H_3$).

14 Claims, 1 Drawing Sheet

DENTAL PORCELAIN SHADING KIT, SYSTEM AND METHOD

This application is a division of application Ser. No. 08/257,411, filed Jun. 9, 1994, now U.S. Pat. No. 5,482,732.

The invention relates to a color-correlation kit and system for a dental porcelain system. The dental porcelain color-correlation system of the invention provides restorations to match a shade guide, the dental porcelain color-correlation kit and system of the invention provides restorations having substantially constant lightness value, from opaque to translucent porcelain.

Ruckert in U.S. Pat. No. 3,360,122 discloses dual-purpose container. Kroder in U.S. Pat. No. 3,628,248 discloses process for forming artificial implants. Mackta in U.S. Pat. No. 3,932,938 discloses a pigment package for dental filling material. Bergen in U.S. Pat. No. 3,956,827 discloses color discrimination test apparatus and method. Roll in U.S. Pat. No. 3,986,777 discloses tristimulus colorimeter for use in the fabrication of artificial teeth. Roll in U.S. Pat. No. 4,096,217 discloses method of using a particular tristimulus colorimeter in making artificial teeth. Alderman in U.S. Pat. No. 4,115,922 discloses dental crown and bridge shading system. Tsai in U.S. Pat. No. 4,132,830 discloses noble-metal dental alloy and dental method. Ingersoll et al in U.S. Pat. No. 4,201,577 disclose ceramic substrate alloy. Jeannette in U.S. Pat. No. 4,207,678 discloses multiple dental shade guide system. Ibsen et al in U.S. Pat. No. 4,294,349 disclose a kit for repair of porcelain dental prostheses. Walker in U.S. Pat. No. 4,386,962 discloses composition and method for producing ceramic articles. Rogers in U.S. Pat. No. 4,427,501 discloses method of manufacture of artificial teeth. Tanaka in U.S. Pat. No. 4,481,227 discloses method of coloring bakeable porcelain dental restorations. Miller in U.S. Pat. No. 4,617,159 discloses method of molding a dental shade sample. Watanabe et al in U.S. Pat. No. 4,626,514 disclose good aesthetic artificial dental materials by calcium phosphate glass-ceramic. Blair et al in U.S. Pat. No. 4,650,418 discloses dental restoration shading. Watanabe et al in U.S. Pat. No. 4,681,633 disclose high strength calcium phosphate glass ceramic materials. Pitre in U.S. Pat. No. 4,793,805 discloses apparatus and method for forming shade samples. Boon in U.S. Pat. No. 4,802,850 discloses dental-porcelain color matching system. Panzera et al in U.S. Pat. No. 4,828,117 disclose porcelain dental restoration having a plurality of uniform, color-matched layers. Tanaka in U.S. Pat. No. 4,997,723 discloses metal-porcelain dental restorations, dental veneers, dental bridges and metal foil for making dental appliances. Giaramita in U.S. Pat. 5,004,417 discloses color dental kit and method of use. Bowen in U.S. Pat. No. 5,057,018 discloses microcrystalline inserts for megafilled composite dental restorations. Tanaka in U.S. Pat. No. 5,076,789 discloses metal-porcelain dental restorations, dental veneers, dental bridges and metal foil for use therein and methods for making dental appliances. McLaughlin in U.S. Pat. No. 5,094,619 discloses coloration of dental restorations. Evans et al in U.S. Pat. No. 5,104,319 disclose method of manufacturing dental restorations. Klepacki in U.S. Pat. No. 5,125,970 discloses material and method for colorizing dental prostheses. Yamaguchi et al in U.S. Pat. No. 5,127,835 disclose process for preparation of dental crown restoration and kit for use in carrying out said process. McLaughlin in U.S. Pat. No. 5,162,130 discloses light activated coloration of dental restorations. Tanaka in U.S. Pat. No. 5,186,626 discloses metal-porcelain dental bridges. Thompson in U.S. Pat. No. 5,240,414 discloses method for shade selection in restorative dentistry.

Unlike systems for making porcelains in accordance with the invention, prior art systems for making porcelains having lightness values for opaque porcelains which are lower than the lightness values for opacious dentin porcelains, as shown in Table 4.

Metal based porcelain dental restorations such as crowns and bridges comprise a metal framework called a "coping", which is covered by several layers of porcelain to simulate the appearance of natural teeth. The porcelain is applied in a plurality of layers, the first layer applied over the coping is called the "opaque porcelain layer", the purpose of which is to hide the metal framework. The second layer applied over the first layer is called the "body or dentin porcelain layer". The body porcelain layer exhibits translucence to a degree similar to that of the dentine layer of natural dentition. In addition, a second layer of "opacious body or dentin" porcelain is used in conjunction with the body porcelain. The opacious body porcelain is more opaque than body porcelain layer and is preferably used under the body porcelain or in place of the body porcelain where the restoration is very thin. Preferably an incisal porcelain layer is positioned over the body porcelain layer. The incisal porcelain layer has a translucency approximately equal to the translucency of the enamel layer of natural dentition. The outer surface is either glazed with a very thin transparent layer, or it is baked or polished to a high gloss.

Color is imparted to a metal-based porcelain dental restoration by coloring the opaque and body porcelain layers. It is an objective in the production of dental restorations to make the restoration resemble as closely as possible the patient's natural teeth.

Recently, all-ceramic dental restorations have been introduced commercially. These restorations replace the metal coping with a ceramic base, and because the metal base is eliminated, they can be made to more closely resemble natural dentition. But even with an all-ceramic restoration, there is obviously still a need to match the color of the patient's natural teeth. One way to color an all-ceramic restoration is to color the ceramic base by any of several techniques (e.g., the color may be incorporated in the base material itself, or the base may be stained with a porcelain stain). The body porcelain, an incisal layer and a glaze are fired, as is the case with metal-based restorations.

Whether the porcelain restoration has a metal base or is all ceramic, its apparent color is influenced by the color of the body porcelain layer and by the color of the layer just beneath the body porcelain. The incisal porcelain and glaze layers contribute little, if anything, to the perceived color of the restoration because they are quite translucent or transparent, and are, at most, only slightly colored. Since natural teeth have translucent layers, i.e., enamel and dentine, the restoration must have translucent layers on its surface to match as closely as possible the appearance of natural teeth. However, the translucency of the body porcelain layer complicates the task of matching the color of natural teeth. The thickness of the body porcelain varies from a rather thick layer in the middle to a thin layer at the gingival or incisal end of the restoration. Thus, it is normal for the body porcelain layer thickness to vary from about ¼ to 1½ millimeters. Because of this variation in thickness, light penetrates the body porcelain layer to different depths before it is reflected back to the observer, and unless the layer just beneath is exactly the same color as the body porcelain, the apparent color of the restoration will vary over its surface with the thickness of the body porcelain.

Thus, the visually discerned color of an opaque object is determined by the amount of visible illuminating light reflected (from the surface of the object) to the observer. The perceived color of a porcelain dental restoration is mainly the result of the diffuse reflectance from the translucent body porcelain layer covering an underlying more opaque layer. Perceived color is thus a combination of the scattered and reflected color of the translucent layer plus the color reflected from the underlying layer. When the translucent layer varies in thickness, the amount of color contribution from the underlying layer will vary inversely with the thickness of the translucent layer. Therefore, unless the translucent layer and the underlying layer are closely related in color, the perceived color of the restoration will be dependent upon the thickness of the body porcelain layer.

Accordingly, it is clear that it is desirable to provide porcelain dental restorations in which the body porcelain matches the color of the layer beneath. Heretofore, however, there has been no commercial dental porcelain restoration kits in which the body porcelain material, when fired, matched exactly the hue, chroma and lightness of the fired ceramic material of the layer just beneath. The resulting prior aft restorations do not match the hue, chroma or value of the corresponding shade guide component. In order to compensate for this, the dental technician has often had to modify the color of the opaque and body porcelain or apply porcelain stains to different portions of the restoration to prevent the perceived color from varying to an undesirable degree from a preselected color of a shade guide. This was not only a time consuming task, but also the results were quite dependent upon the skill of the technician.

According to the invention, porcelain is produced having a predetermined hue, chroma and lightness to match the hue, chroma and lightness of an underlying, more opaque, layer. Preferably, an observer cannot visually discern any difference in hue, chroma and lightness in a composite including a layer of the translucent porcelain overlying the underlying layer, even though the translucent porcelain layer varies in thickness.

It is an object of the invention to provide a kit for the preparation of porcelain dental restorations having a layer of translucent porcelain overlying a more opaque ceramic layer. The kit includes at least one labeled container of colored translucent porcelain powder and at least one labeled container of ceramic material for the more opaque layer, and when the translucent porcelain powder and ceramic material for the more opaque layer are fired, the colors of the translucent porcelain and the more opaque ceramic layer match spectrophotometrically such that the two colors have less than 5 degrees difference in CIE hue angle.

It is an object of the invention to provide a system of dental porcelain powders for making crowns and bridges having a translucent porcelain layer over an opaque ceramic layer, which includes a set of powders having a translucent powder having a translucent hue when formed into the translucent porcelain layer, and an opaque powder having an opaque hue when formed into the opaque ceramic layer, wherein the translucent hue is within 5 degrees of CIE psychometric hue angle of the opaque hue. In the dental restoration of the invention, the color-matched layers are both uniform and match each other. "CIE L*a*b* units" as used herein refers to CIE L*a*b* units according to the 1976 standard.

"Porcelain", as used herein and in the dental restoration arts, refers to the ceramic materials used to cover the base or coping in a restoration such as a crown or bridge. An important function of the porcelain in a dental restoration is to provide the aesthetic appearance of natural dentition.

"Ceramic", as used herein, includes the porcelain materials used in a dental restoration, as defined above, and also includes the ceramic base of an all-ceramic dental restoration.

"Uniform color layer" as used herein means that the layer has substantially equal hue, chroma and lightness throughout and is free of porcelain stains or the like applied to only a portion of the surface of the layer to compensate for the failure of the two layers to match in color.

"Matching in color", as used herein, means that when a composite is made having the translucent porcelain layers overlying the more opaque ceramic layer, an observer cannot visually discern any non-uniformity in the substantially equal hue, chroma and lightness of the composite even though the thickness of the translucent porcelain layer may vary over the normal range of thicknesses for the body porcelain layer in a porcelain dental restoration (e.g., from about one-half millimeter to about one and one-half millimeters). When color is matched the infinite optical thicknesses of the translucent porcelain are the same as the opaque porcelain.

BRIEF SUMMARY OF THE INVENTION

Figure 1:
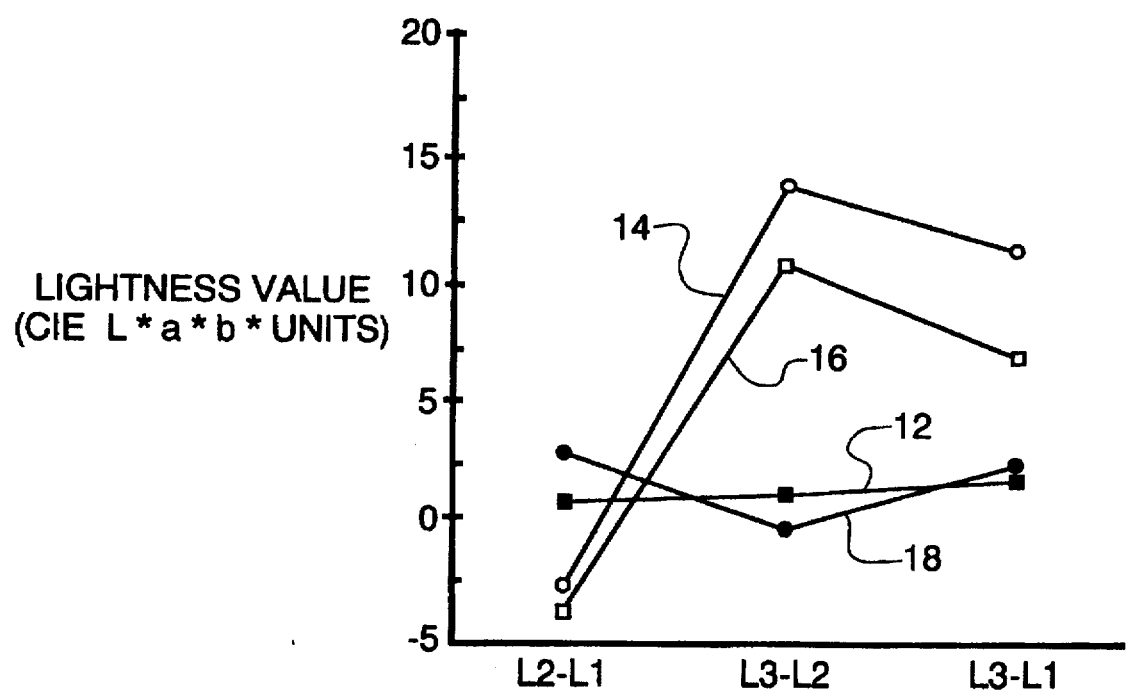
FIG. 1 is a graphic presentation of the difference in lightness value for dentin, opacious dentin and opaque porcelain layers formed from powders of the invention, and from prior art powders listed in Table 5.

The invention provides a kit, system and method for the preparation of porcelain dental restorations. First, second and third powders are provided in labeled containers. The first powder has a lightness value ($L_1$) when formed into a least opaque porcelain layer. The second powder has a lightness value ($L_2$) when formed into a less opaque ceramic layer. The third powder has a lightness value ($L_3$) when formed into a most opaque ceramic layer. The third lightness value is greater than the second lightness value, which is greater than the first lightness value. The lightness value differences between the third lightness value ($L_3$) and the first lightness value ($L_1$) are less than 2.5 CIE L*a*b* units. Preferably, the first powder has a first hue ($H_1$) when formed into the least opaque porcelain layer, the second powder has a second hue ($H_2$) when formed into the less opaque ceramic layer, and the third powder has a third hue ($H_3$) when formed into the most opaque ceramic layer. Preferably the first hue ($H_1$) and the second hue ($H_2$) are within 5 degrees of the CIE psychometric hue angle of the third hue ($H_3$).

DETAILED DESCRIPTION OF THE INVENTION

The invention provides a kit and system for the preparation of porcelain dental restorations. In accordance with a preferred embodiment of the invention a system of dental porcelain powders provided for making crowns and bridges having a translucent porcelain layer over an intermediate ceramic layer over an opaque ceramic layer. The kit and system include a first set of powders having a first, a second and a third powder. Preferably the kit and system include a second set of powders having a first, a second and a third powder.

The first powder has a first opacity ($O_1$), a first hue ($H_1$), first chroma ($C_1$) and first lightness value ($L_1$) when formed into the translucent porcelain layer. The second powder has a second opacity ($O_2$), a second hue ($H_2$), second chroma ($C_2$) and second lightness value ($L_2$) when formed into the intermediate ceramic layer. The third powder has a third opacity ($O_3$), a third hue ($H_3$), third chroma ($C_3$) and third lightness value ($L_3$) when formed into the opaque ceramic layer. The third opacity ($O_3$) is greater than the second opacity ($O_2$) which is greater than the first opacity ($O_1$).

Preferably for each set of powders the third lightness value ($L_3$) is greater than the second lightness value ($L_2$) and the second lightness value ($L_2$) is greater than the first lightness value ($L_1$). The lightness value differences between the third lightness value ($L_3$) and the first lightness value ($L_1$) is preferably less than 2.5 CIE L*a*b* units and more preferably less than 2 CIE L*a*b* units. Each of the first hue ($H_1$) and the second hue ($H_2$) are within 5 degrees of the CIE psychometric hue angle of the third hue ($H_3$).

In accordance with a preferred embodiment of the invention is provided a system of dental porcelain color matching by measuring reflectance of visible light from the outer surface of a comparative dental porcelain article at a plurality of wavelengths. A translucent powder is formed into a dental porcelain layer having an outer surface having a percent reflectance for each of a plurality of visible light wavelengths. At each wavelength the translucent layer percent reflectance is different from the articles-percent reflectance by a substantially constant percentage.

The invention provides a shading system with a color-correlation scheme to make coordinated shades of porcelains of varied translucency. Such porcelains are combined to make a dental restoration corresponding to one dental shade reference article. In accordance with the invention is provided greater fidelity in hue between the materials to be sequentially applied to form dental ceramic products.

In accordance with a preferred embodiment of the invention dental technicians use at least two, and often three porcelain powders to create a crown or bridge. An opaque porcelain powder is always used to hide a metal understructure. Dentin and opacious dentin porcelains are fired on top of the opaque porcelains to create the tooth anatomy. These latter porcelains are translucent. After firing, the tooth must visually match the shade guide tab designated in a dentist's prescription.

Prior art color-coordination has been limited to matching the chroma and lightness of the opaque and body porcelains. However, color matching depends on the hue, as well as, the chroma and the lightness. Color coordinates of translucent materials are dependent on the thickness of the sample unless the samples are thicker than the "infinite optical thickness". In the system of the present invention all three color coordinates are used and the colors are matched with samples based on the infinite optical thickness.

In accordance with the invention to correlate the shades of the translucent porcelains, shaded porcelain powders are made of three transparencies. The infinite optical thickness of the most transparent porcelain is separately determined by making fired samples of progressively greater thicknesses. The color coordinates and the reflectivity of the sample for visible light transmitted to the sample at each of several individual wavelengths (preferably at ten or more wavelengths between 400 and 700 mm) is measured with a Datacolor spectrophotometer. Preferably these wavelengths are uniformly distributed over the range of wavelengths transmitted by the sample. Eight millimeters thickness is selected to approximate the infinite optical thickness. That is, at this thickness and thicker, the color coordinates and the reflectivity of the samples change very little, no matter whether the background is white or black.

Next, samples of each of the three white porcelains are pressed and fired. The scattering-to-absorption ratio, K/S, of these samples are measured at sixteen visible wavelengths of light using a Datacolor spectrophotometer. Next, pigments are added to one of the translucent porcelain powders. The pigments are adjusted until fired samples of the porcelain visually (or spectrophotometrically) match a shade guide tab. These samples are made of approximately the same thickness. After the visual match (or spectrophotometric percent reflective match at a plurality of wavelengths) of one translucent porcelain is obtained, a thicker sample of the porcelain is made, at the approximate infinite optical thickness. The K/S is measured for this pigmented porcelain sample. The K/S is calculated for the remaining two porcelains, by maintaining the difference in the K/S measured for the white porcelains, as shown in Table 1.

TABLE 1

| Wavelength (nm) | K/S WHITE opaque | K/S WHITE opaque dentin | K/S WHITE dentin | delta K/S op. op. dent. | delta K/S dentin | K/S Pigmented Opaque | K/S Pigmented Op. Dentin | K/S Pigmented Dentin |
|---|---|---|---|---|---|---|---|---|
| 400 | 0.01211 | 0.28381 | 0.31660 | −0.27170 | −0.30449 | 1.18445 | 1.45615 | 1.48894 |
| 420 | 0.00414 | 0.22646 | 0.31454 | −0.22232 | −0.31040 | 1.01788 | 1.24020 | 1.32828 |
| 440 | 0.00306 | 0.20855 | 0.31557 | −0.20549 | −0.31251 | 0.88677 | 1.09226 | 1.19928 |
| 460 | 0.00253 | 0.20438 | 0.32020 | −0.20185 | −0.31767 | 0.78074 | 0.98259 | 1.09841 |
| 480 | 0.00224 | 0.20047 | 0.32908 | −0.19823 | −0.32684 | 0.63609 | 0.83432 | 0.96293 |
| 500 | 0.00199 | 0.19366 | 0.33512 | −0.19167 | −0.33313 | 0.48660 | 0.67827 | 0.81973 |
| 520 | 0.00160 | 0.19044 | 0.34147 | −0.18884 | −0.33987 | 0.38370 | 0.57254 | 0.72357 |
| 540 | 0.00138 | 0.18505 | 0.34363 | −0.18367 | −0.34225 | 0.31296 | 0.49663 | 0.65521 |
| 560 | 0.00166 | 0.18621 | 0.35099 | −0.18455 | −0.34933 | 0.26690 | 0.45145 | 0.61623 |
| 580 | 0.00163 | 0.19109 | 0.35408 | −0.18946 | −0.35245 | 0.23600 | 0.42546 | 0.58845 |
| 600 | 0.00175 | 0.18888 | 0.36916 | −0.18713 | −0.36741 | 0.18951 | 0.37664 | 0.55692 |
| 620 | 0.00141 | 0.18916 | 0.38535 | −0.18775 | −0.38394 | 0.16970 | 0.35745 | 0.55364 |
| 640 | 0.00184 | 0.19763 | 0.41139 | −0.19579 | −0.40955 | 0.15720 | 0.35299 | 0.56675 |
| 660 | 0.00138 | 0.19914 | 0.42334 | −0.19776 | −0.42196 | 0.15170 | 0.34946 | 0.57366 |
| 680 | 0.00171 | 0.20467 | 0.44080 | −0.20296 | −0.43909 | 0.16341 | 0.36637 | 0.60250 |
| 700 | 0.00183 | 0.20648 | 0.45645 | −0.20465 | −0.45462 | 0.14250 | 0.34715 | 0.59712 |
|  | measured | measured | measured | calculated | calculated | measured | calculated | calculated |

The K/S values are converted to reflectivity using equation 1, where r is the reflectivity at each wavelength for which K/S is calculated.

$$K/S = (1-r)^2/2r \qquad (1)$$

The tristimulus values of the other two porcelains are calculated, as in Table 2, from the product of the reflectivity at the sixteen wavelengths and the spectral power and observer functions in Table 3.

John Wiley & Sons, 1975, especially pages 139–169, for discussions of the methods used to calculate CIE tristimulus values. Briefly, the CIE tristimulus values are obtained from the spectrophotometric data by multiplying, wavelength by

TABLE 2

| R Pigmented Opaque (percent) | R Pigmented Op. Dentin | R Pigmented Dentin | R*Px Pigmented Dentin | R*Py Pigmented Dentin | R*Pz Pigmented Dentin | R*Px Pigmented Op. Dentin | R*Py Pigmented Op. Dentin | R*Pz Pigmented Op. Dentin |
|---|---|---|---|---|---|---|---|---|
| 26.38 | 21.28% | 20.97% | 0.0526 | 0.0048 | 0.2286 | 0.0534 | 0.0049 | 0.2319 |
| 29.05 | 23.56% | 22.57% | 0.7294 | 0.0745 | 3.4718 | 0.7614 | 0.0777 | 3.6239 |
| 30.98 | 25.44% | 24.05% | 1.6063 | 0.2660 | 8.2673 | 1.6995 | 0.2814 | 8.7469 |
| 34.42 | 27.07% | 25.36% | 1.5459 | 0.6644 | 8.9660 | 1.6500 | 0.7092 | 9.5696 |
| 37.70 | 29.66% | 27.38% | 0.4712 | 1.3521 | 4.3529 | 0.5104 | 1.4644 | 4.7143 |
| 41.83 | 33.05% | 29.94% | 0.0177 | 2.5952 | 1.1967 | 0.0195 | 2.8644 | 1.3209 |
| 46.13 | 35.89% | 31.98% | 0.6983 | 4.4273 | 0.3345 | 0.7839 | 4.9696 | 0.3754 |
| 45.77 | 38.31% | 33.62% | 2.2897 | 5.8352 | 0.0797 | 2.6091 | 6.6491 | 0.0908 |
| 52.59 | 39.94% | 34.65% | 4.2152 | 5.9450 | 0.0007 | 4.8593 | 6.8533 | 0.0008 |
| 55.12 | 40.96% | 35.43% | 5.8339 | 5.0124 | −0.0007 | 6.7452 | 5.7953 | −0.0008 |
| 58.37 | 43.05% | 36.36% | 6.2660 | 3.6742 | 0.0000 | 7.4192 | 4.3504 | 0.0000 |
| 60.38 | 43.95% | 36.46% | 4.7013 | 2.1949 | 0.0000 | 5.6666 | 2.6457 | 0.0000 |
| 62.07 | 44.16% | 36.06% | 2.2453 | 0.9330 | 0.0000 | 2.7496 | 1.1425 | 0.0000 |
| 62.56 | 44.33% | 35.86% | 0.7570 | 0.2966 | 0.0000 | 0.9359 | 0.3666 | 0.0000 |
| 62.21 | 43.53% | 35.03% | 0.2007 | 0.0778 | 0.0000 | 0.2494 | 0.0966 | 0.0000 |
| 62.83 | 44.45% | 35.18% | 0.0422 | 0.165 | 0.0000 | 0.0533 | 0.0209 | 0.0000 |
| measured | calculated | calculated | 31.6729 | 33.3699 | 26.8974 | 36.7656 | 38.2920 | 28.6738 |
|  |  |  | $X_D$ | $Y_D$ | $Z_D$ | $X_{oa}$ | $Y_{oo}$ | $Z_{oo}$ |

$L^* = 116*((Y/100)^{(1/3)})-16$
$a^* = 500*((X/94.83)^{(1/3)}-(Y/100)^{(1/3)})$
$b^* = 200*((Y/100)^{(1/3)}-(Z/107.38)^{(1/3)})$

TABLE 3

| Px | Py | Pz |
|---|---|---|
| 0.2510 | 0.0230 | 1.0900 |
| 3.2320 | 0.3300 | 15.3830 |
| 6.6790 | 1.1060 | 34.3760 |
| 6.0960 | 2.6200 | 35.3550 |
| 1.7210 | 4.9380 | 15.8970 |
| 0.0590 | 8.6680 | 3.9970 |
| 2.1840 | 13.8460 | 1.0460 |
| 6.8100 | 17.3550 | 0.2370 |
| 12.1650 | 17.1570 | 0.0020 |
| 16.4670 | 14.1480 | −0.0020 |
| 17.2330 | 10.1050 | 0.0000 |
| 12.8940 | 6.0200 | 0.0000 |
| 6.2260 | 2.5870 | 0.0000 |
| 2.1110 | 0.8270 | 0.0000 |
| 0.5730 | 0.2220 | 0.0000 |
| 0.1200 | 0.0470 | 0.0000 |

The tristumulas values, x, y, and Z are used to calculate the CIE coordinates L*a*b. From the color coordinates, and calibration data for the pigments, formulas are made that have the color coordinates desired. Such a system predicts an opaque and opacious dentin porcelains chroma leads to "color from within" and the visual results are very satisfactory. The principles underlying the utilization of CIE tristimulus values and their calculation from the spectral response of a given color are known to those skilled in the art of color analysis. For instance, see Billmeyer and Saltzman, PRINCIPLES OF COLOR TECHNOLOGY, Second Edition, John Wiley & Sons, 1981, especially pages 44–46, 80–83, and 174, and Judd and Wyszecki, COLOR IN BUSINESS, SCIENCE AND INDUSTRY, Third Edition, wavelength, the spectral reflectance of the sample (R), the relative spectral power of the illuminant, and the values of the respective CIE standard observer functions ($P_{x1}P_{y1}P_z$). These products are then added up for all the wavelengths in the visible region of the spectrum. Tables are available that give the products of the CIE standard observer functions and the spectral power for various CIE illuminants (e.g., daylight, incandescent, and fluorescent) for each wavelength. These tables are used to calculate the tristimulus values for standard daylight, incandescent, and fluorescent light sources for the sample under evaluation. From the tristimulus values the CIE L*a*b* coordinates are calculated as in equations (2 –4) as follows:

$$L^*=116* ((Y/100)^{(1/3)})-16 \qquad (2)$$

$$a^*=500*((X/94.83)^{(1/3)}-(Y/100)^{(1/3)}) \qquad (3)$$

$$b^*=200*((Y/100)^{(1/3)}-(Z/107.38)^{(1/3)}) \qquad (4)$$

One trio of porcelains is prepared as described above and compared to prior art porcelains sold as Vita Omega from Vita, Inc., Will-Ceram from Williams, Inc., and Ceramco II from Ceramco, Inc. Values of lightness (L*), hue (h*) and chroma (C*) and the differences therein for dentin, opacious dentin and opaque porcelain layers are shown in Table 4, for ceramic formed from a system of dental porcelain powders of the present invention and ceramics formed from systems of prior art dental porcelain powders sold by Ceramco II, Vita-Omega and Will Ceram.

TABLE 4

| | | Lightness Value (L) | | Difference | | Hue (h) | | Difference | | Chroma (C) | | Difference |
|---|---|---|---|---|---|---|---|---|---|---|---|---|
| PRESENT INVENTION | | | | | | | | | | | | |
| dentin | L1 | 75.44 | L2–L1 | 1.00 | h1 | 83.32 | h2–h1 | −1.53 | C1 | 19.14 | C2–C1 | 1.03 |
| opacious dentin | L2 | 76.44 | L3–L2 | 1.15 | h2 | 81.79 | h3–h2 | −3.32 | C2 | 20.17 | C3–C2 | 1.83 |
| opaque | L3 | 77.59 | L3–L1 | 2.15 | h3 | 78.47 | h3–h1 | −4.85 | C3 | 22.00 | C3–C1 | 2.86 |
| PRIOR ART-Ceramco II | | | | | | | | | | | | |
| dentin | L1 | 71.78 | L2–L1 | 2.90 | h1 | 83.31 | h2–h1 | −2.91 | C1 | 14.13 | C2–C1 | 1.82 |
| opacious dentin | L2 | 74.68 | L3–L2 | −0.22 | h2 | 80.40 | h3–h2 | −1.02 | C2 | 15.95 | C3–C2 | 2.41 |
| opaque | L3 | 74.46 | L3–L1 | 2.68 | h3 | 79.38 | h3–h1 | −3.93 | C3 | 18.36 | C3–C1 | 4.23 |
| PRIOR ART-Vita Omega | | | | | | | | | | | | |
| dentin | L1 | 73.22 | L2–L1 | −3.58 | h1 | 77.74 | h2–h1 | −1.07 | C1 | 16.05 | C2–C1 | 10.27 |
| opacious dentin | L2 | 69.66 | L3–L2 | 10.97 | h2 | 76.67 | h3–h2 | 1.58 | C2 | 26.32 | C3–C2 | −6.75 |
| opaque | L3 | 60.63 | L3–L1 | 7.41 | h3 | 78.25 | h3–h1 | 0.51 | C3 | 19.57 | C3–C1 | 3.52 |
| PRIOR ART-Will Ceram | | | | | | | | | | | | |
| dentin | L1 | 71.86 | L2–L1 | −2.56 | h1 | 84.15 | h2–h1 | −1.89 | C1 | 17.57 | C2–C1 | 1.18 |
| opacious dentin | L2 | 69.30 | L3–L2 | 14.16 | h2 | 82.26 | h3–h2 | −5.47 | C2 | 18.75 | C3–C2 | 0.27 |
| opaque | L3 | 63.46 | L3–L1 | 11.60 | h3 | 76.78 | h3–h1 | −7.36 | C3 | 19.02 | C3–C1 | 1.45 |

Hue is the angle measured from the horizontal each point creates when connected to the origin of the graph of b* verses a*, and is found mathematically from equation 5. Chroma is the distance of each point from the origin, and is found mathematically from equation 6. Mathematically hue and chroma are expressed as:

$$Hue = \tan^{-1}(b^*/a^*) \tag{5}$$

$$Chroma = \sqrt{(a^{*2}+b^{*2})} \tag{6}$$

For the Vita Omega porcelain, the lightness is highest for the opaque and usually lowest for the dentin porcelain. For Ceramco II porcelains, the lightness is highest for the opacious dentin porcelains and the opaque and dentin porcelains are similar. Porcelains made in accordance with the invention have lightness values (L) that decrease from the opaque to more translucent opacious dentin and dentin porcelains. Unlike systems for making porcelains in accordance with the invention, prior art systems for making porcelains having lightness values for opaque porcelains which are lower than the lightness values for opacious dentin porcelains, as shown in Table 4.

Consistency for hue, chroma and lightness value is provided in porcelains made in accordance with the invention. Thus, the invention provides prematched shades for use in making porcelains products having consistent hue, chroma and lightness values.

X, Y and Z respectively are the sums shown in Table 2.

The invention provides color matching sets of ceramic powder, one powder being the material for a translucent porcelain and the another powder being the material for a ceramic having a lesser degree of translucency than the porcelain, such that, when the powders are fired, the porcelain match in color. The powders provided by the invention may be in the form of dry powders, or they may be premixed with a liquid (originally aqueous based) to form a paste.

FIG. 1 shows the differences in lightness values from Table 4 including line 12 for ceramic layers formed from powders in accordance with the invention. The lightness values of the ceramic layers formed from powders in accordance with the invention increase from a layer formed from a most opaque powder to a layer formed from a less opaque powder to a layer formed from a least opaque powder.

The change in lightness value is substantially monotonic. By contrast the lines for differences in lightness values 14, 16 and 18 for ceramic layers formed from prior art powders are substantially not monotonic.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A kit combination for the preparation of porcelain dental restorations having a most opaque ceramic layer underlying a less opaque ceramic layer positioned beneath a least opaque porcelain layer, comprising:

a first powder enclosed by a first labeled container and having a first opacity ($O_1$), and a first lightness value ($L_1$) when formed into said least opaque porcelain layer, a second powder enclose by a second labeled container having a second opacity ($O_2$) and a second lightness value ($L_2$) when formed into said less opaque ceramic layer, and a third powder enclosed by a third labeled container having a third opacity ($O_3$) and a labeled container having a third opacity ($O_3$) and a third lightness value ($L_3$) when formed into said most opaque ceramic layer, said third opacity ($O_3$) being greater than said second opacity ($O_2$), said second opacity ($O_2$) being greater than said first opacity ($O_1$), said third lightness value ($L_3$) being greater than said second lightness value ($L_2$) and said second lightness value ($L_2$) being greater than said first lightness value ($L_1$).

2. The kit of claim 1 wherein said third opacity ($O_3$) is 100 percent opaque.

3. The kit of claim 2 wherein said second opacity ($O_2$) is from 94 percent to 99 percent opaque.

4. The kit of claim 2 wherein said first powder has a first chroma ($C_1$) and said third powder has a third chroma ($C_3$) and said third chroma ($C_3$) and said first chroma ($C_1$) have a difference in chroma of less than 3 CIE L*a*b* units.

5. The kit of claim 1 wherein said third lightness value ($L_3$) and said first lightness value ($L_1$) have a difference in lightness value of less than 2.5 CIE L*a*b* units.

6. The kit of claim 1 wherein said first powder has a first hue ($H_1$) when formed into said least opaque porcelain layer, said second powder has a second hue ($H_2$) when formed into said less opaque ceramic layer, said third powder has a third hue ($H_3$) when formed into said most opaque ceramic layer, each of said first hue ($H_1$) and said second hue ($H_2$) being within 5 degrees of the CIE psychometric hue angle of said third hue ($H_3$).

7. The kit of claim 1 wherein said first, second and third powder each comprises an inorganic pigment.

8. The kit combination of claim 1 wherein said powders are formed into crowns or bridges.

9. The kit of claim 8 wherein the lightness value difference between said third lightness value ($L_3$) and said first lightness value ($L_1$) are less than 2.5 CIE L*a*b units.

10. The kit of dental porcelain powders of claim 8 wherein said first powder has a first hue ($H_1$) when formed into said least opaque porcelain layer, said second powder has a second hue ($H_2$) when formed into said less opaque ceramic layer, said third powder has a third hue ($H_3$) when formed into said most opaque ceramic layer, each of said first hue ($H_1$) and said second hue ($H_2$) being within 5 degrees of the CIE psychometric hue angle of said third hue ($H_3$).

11. The kit of dental porcelain powders of claim 8 wherein said first powder has a chroma ($C_1$) when formed into said least opaque porcelain layer, said second powder has a chroma ($C_2$) when formed into said less opaque ceramic layer, said third chroma ($C_3$) when formed into said most opaque ceramic layer, each of said third chroma ($C_3$) being greater than said second chroma ($C_2$) and said second chroma ($C_2$) being greater than said first chroma ($C_1$), and the difference between said third powder has a chroma ($C_3$) and said first chroma ($C_1$) being less than 10 CIE L*a*b* units.

12. The kit of dental porcelain powders of claim 8 further comprising a second set of powders, said second set of powders comprising a first powder ($P_{1s}$) having a first lightness value ($L_{1s}$) when formed into said least opaque porcelain layer, a second powder ($P_{2s}$) having a second lightness value ($L_{2s}$) when formed into said less opaque ceramic layer, a third powder ($P_{3s}$) having a third lightness value ($L_{3s}$) when formed into said most opaque ceramic layer, said first lightness value ($L_{1s}$) being less than said second lightness value ($L_{2s}$) by less than 3 CIE L*a*b* units and said first lightness value ($L_{1s}$) being less than said third lightness value ($L_{3s}$) by less than 3 CIE L*a*b units.

13. The kit of dental porcelain powders of claim 12 wherein said second set first powder ($P_{1s}$) has a first ($H_{1s}$) hue when formed into said least opaque porcelain layer, said second set second powder ($P_{2s}$) has a second hue ($H_{2s}$) when formed into said less opaque ceramic layer, said second set third powder ($P_{3s}$) has a third hue ($H_{3s}$) when formed into said most opaque ceramic layer, said first hue ($H_{1s}$) being within 5 degrees of CIE psychometric hue angle of said second hue ($H_{2s}$) and said first hue ($H_{1s}$) being within 5 degrees of CIE psychometric hue angle of said third hue ($H_{3s}$).

14. The kit of dental porcelain powders of claim 12 wherein said second set third lightness value ($L_{3s}$) is greater than said second set second lightness value ($L_{2s}$) and said second set second lightness value ($L_{2s}$) is greater than said second set first lightness value ($L_{1s}$).

* * * * *